(12) United States Patent
Ritter et al.

(10) Patent No.: US 7,513,964 B2
(45) Date of Patent: Apr. 7, 2009

(54) REAL-TIME INFRARED THERMOGRAPHY INSPECTION AND CONTROL FOR AUTOMATED COMPOSITE MARTERIAL LAYUP

(75) Inventors: John A. Ritter, Wichita, KS (US); John F. Sjogren, Wichita, KS (US)

(73) Assignee: The Boeing Company, Chicago, IL (US)

( * ) Notice: Subject to any disclaimer, the term of this patent is extended or adjusted under 35 U.S.C. 154(b) by 417 days.

(21) Appl. No.: 11/067,031

(22) Filed: Feb. 28, 2005

(65) Prior Publication Data

US 2006/0191622 A1 Aug. 31, 2006

(51) Int. Cl.
*B32B 41/00* (2006.01)
(52) U.S. Cl. .................... 156/64; 250/341.6; 250/341.8
(58) Field of Classification Search .................... 156/64, 156/361, 378, 379, 366, 367; 250/341.6, 250/341.8
See application file for complete search history.

(56) References Cited

U.S. PATENT DOCUMENTS

| | | | |
|---|---|---|---|
| 6,419,387 B1 | 7/2002 | Legrandjacques et al. | 374/5 |
| 6,591,021 B1 | 7/2003 | Breiter et al. | |
| 6,730,912 B2 | 5/2004 | Sun et al. | 250/341.6 |
| 2002/0141632 A1* | 10/2002 | Engelbart et al. | 382/141 |
| 2003/0137593 A1 | 7/2003 | Watanabe et al. | |
| 2003/0145932 A1* | 8/2003 | Holmes et al. | 156/64 |

OTHER PUBLICATIONS

R. J. Maqueda, G. A. Wurden, J. L. Terry and J. Gaffke, "Digital-Image Capture System For The IR Camera Used in Alcator C-Mod", Review of Scientific Instruments, vol. 72, No. 1, Jan. 2001, pp. 927-930.
Gregory R. Stockton, Advances in Selected Application and Methodology for Aerial Infrared Thermography, 13 pgs.
Xavier Maldague, Applications of Infrared Thermography in Nondestructive Evaluation, 23 pgs.
K. Elliott Cramer, NASA Thermographic Inspection of Advanced Composite Materials. 7 pgs.
Products & Application, 6 pgs.
A Historical Perspective, 3 pgs.
X. Maldague, Introduction to NDT by Active Infrared Thermography, 22 pgs.R. B. Dinwiddie and B. J. Frame, Composite Manufacturing NDE Using Active Infrared Thermography, 6 pgs.
Infrared Thermography, 5 pgs.
R. B. Dinwiddie and B. J. Frame, Composite Manufacturing NDE Using Active Infrared Thermography.

* cited by examiner

*Primary Examiner*—George R Koch, III
(74) *Attorney, Agent, or Firm*—Baker Hostetler LLP (57) ABSTRACT

A real-time thermal imaging apparatus and method includes multiple digital infrared cameras mounted to an automated composite material layup device to record digital infrared images of the composite material surface on a real-time basis during a composite material layup process. The digital infrared cameras are triggered periodically to produce digital images of the composite material. The digital image data is sent to an image analyzer which detects edges of and anomalies in the composite material and generates alarm and other process control signals. The image analyzer also aggregates the digital images from the multiple cameras and the digital images recorded over a sequence in time to produce a continuous virtual digital image of the composite material surface. The digital image data and associated analysis results are saved and may be displayed on a real-time basis or at a later time.

25 Claims, 6 Drawing Sheets

REAL-TIME INFRARED THERMOGRAPHY INSPECTION AND CONTROL FOR AUTOMATED COMPOSITE MARTERIAL LAYUP

FIELD OF THE INVENTION

The present invention relates generally to nondestructive in-process inspection or evaluation. More particularly, the present invention relates to infrared thermography inspection of composite materials during layup, prior to consolidation and cure.

BACKGROUND OF THE INVENTION

Graphite fiber reinforced epoxy composites are playing an important role in the production of critical aerospace structures and primary structures of commercial aircraft. These graphite/epoxy composite material products are often fabricated from resin-impregnated cloth, mat or filaments in flat form known as prepreg. After the initial fabrication, or layup, process composite materials generally are inspected to identify flaws in the composite material, as well as to verify that the material edges are within tolerance.

For aerospace products made from composite materials it is important that flaws and out of tolerance conditions are prevented from entering the consolidation and cure stages. This is to reduce the cost of repair or complete rejection of the product. Manual inspection to perform this task during layup can be very labor intensive and problematic. Composite material flaws can include wrinkles, disbonds, inclusions, and porosity. Many out of specification conditions such as excessive gaps, splices, resin or fiber cannot be effectively detected after cure by non-destructive techniques and must be prevented or detected for correction during layup.

A method currently used to inspect composite materials involves visual imaging of the material surface. The images are processed to detect shadows and reflections on the surface in order to detect wrinkles, Foreign Object Debris (FOD), and material edges. However, machine clearance and the width of the material can make the desired lighting angle difficult or impossible to obtain. Furthermore, this method is not successful in detecting non-adhered material or inclusions, which produce minimal changes in the composite material surface.

Another method of inspection involves processing a visual image of a laser-produced line to detect variations in the height of the composite material surface in order to detect wrinkles and material edges. However, this method requires precise control of distance to and alignment with the material surface, making the method susceptible to vibrations during fabrication processes. This method also is not successful in detecting non-adhered material or thin inclusions, which produce extremely small height variations.

It would be useful to identify composite material edges on and below the surface and to evaluate material defects and foreign material inclusions with reference to the material edge locations using a process that is not highly sensitive to machine vibration or lighting angle. It would also be useful to perform the inspection and evaluation during the initial material laydown fabrication process in order to reduce rework and prevent product rejection, as well as to provide automatic control of fabrication devices. Accordingly, it is desirable to provide a method and apparatus that perform real-time nondestructive inspection of a composite material during fabrication and provide automatic control of a fabrication device.

SUMMARY OF THE INVENTION

The foregoing needs are met, to a great extent, by the present invention, wherein in one aspect a method and apparatus are provided that in some embodiments perform real-time infrared thermal imaging of a composite material during an automated fabrication layup process and provide control signals to a fabrication device, which is not susceptible to machine vibrations, and is capable of detecting slight variations in material surface and subsurface characteristics.

In accordance with one aspect of the present invention, a nondestructive in-process inspection method for automated composite material layup includes generating a control signal to control a digital infrared camera, and sending the control signal to the digital infrared camera. The method further includes digitally imaging an infrared spectral radiance of an area of a surface of a composite material and sending an image data frame to an image analyzer. The image analyzer performs the steps of defining a region of interest (ROI) associated with the surface of the composite material, determining a threshold value associated with the region of interest, and analyzing the image data frame to compare a gray level value to the threshold value.

In accordance with another aspect of the present invention, the nondestructive in-process inspection method for automated composite material layup includes generating either an alert signal or a control signal based on the comparison of the gray level value with the threshold value, and sending the control signal to a composite material placement device controller.

In accordance with yet another aspect of the present invention, a nondestructive in-process inspection device for automated composite material layup includes an automated composite material layup device to place a composite material onto a manufacturing tool, a heat source to apply heat to the composite material, and a plurality of digital infrared cameras attached to the automated composite material layup device to record thermal images of the composite material after the composite material is placed on the manufacturing tool. The in-process inspection device also includes an image analyzer coupled to the digital infrared cameras to define a region of interest (ROI) associated with the surface of the composite material, determine a threshold value associated with the region of interest, analyze the image data frame to compare a gray level value the threshold value, and aggregate at least two digital images to form a single continuous virtual image of the composite material surface.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Infrared thermal imaging, also known as thermography or photothermal inspection, methods and devices make it possible to perform nondestructive testing of a material to detect defects, variations in the properties of the material, or differences in thickness of a coating or layer of the material. Infrared thermal imaging can detect local variations in thermal diffusivity or thermal conductivity at or beneath the surface of the material. Photothermal inspection can be used on metals, such as ferrous materials, including steel, or on non-metallic materials, such as plastics, ceramics, or composite materials.

Typically, the surface of the material is heated, for example with a laser or flash heating, and after a fixed period of time, a thermal image is taken of the surface of the material. An infrared camera images the infrared spectral radiance from the surface of the material, which is representative of the temperature of the surface of the material. Differences in temperature of the surface of the material indicate differing thermal characteristics of the material. These variations in thermal characteristics of the material indicate a possible material defect or the inclusion of a foreign material.

An embodiment in accordance with the present invention provides a method and apparatus for real-time thermal imaging inspection of a composite material during automated fabrication layup. The method and apparatus include a trigger mechanism for digital thermal imaging of the composite material surface. The digital image data is sent to an image analyzer for edge detection and anomaly detection. In addition, digital images over a time sequence or from multiple infrared digital cameras are aggregated to form a continuous virtual image of the composite material surface. The digital image data is saved and a location or outline of defects or anomalies may be graphically displayed or graphically projected onto the composite material surface, such as through the use of a laser projector or image projector.

Figure 1:
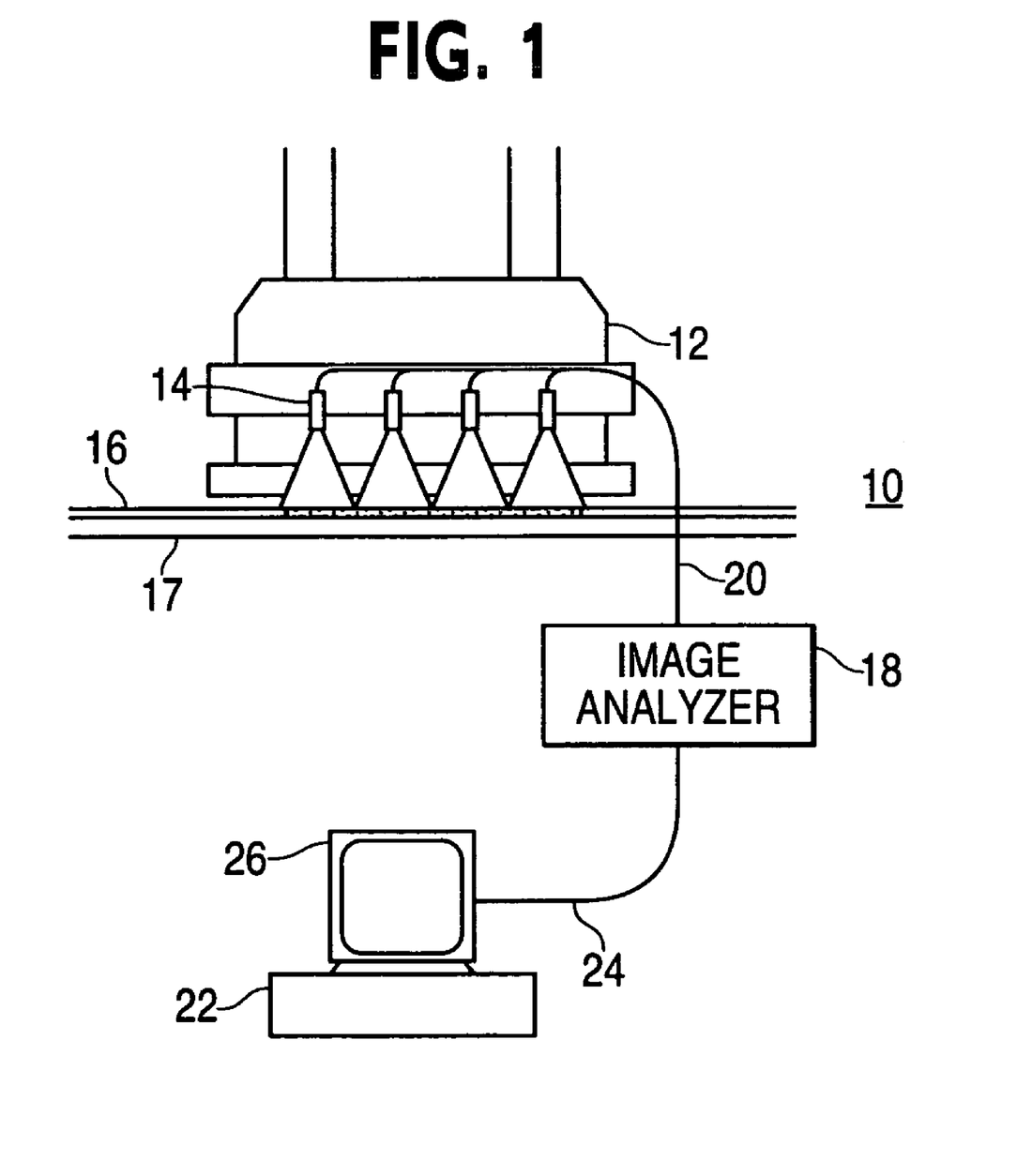
FIG. 1 is a diagram of a real-time thermal imaging system according to a preferred embodiment of the invention.

An embodiment of the present inventive method and apparatus will now be described with reference to the drawing figures, in which like numerals refer to like parts throughout. An embodiment of the present inventive apparatus and method is illustrated in FIG. 1, which illustrates a real-time thermal imaging system 10. The real-time thermal imaging (RTTI) system 10 includes an automatic composite material layup device 12 to which are attached multiple digital infrared cameras 14. An example of a type of digital infrared camera 14 suitable for use with an embodiment of the invention includes a focal plane array (FPA) device, which in effect is a spectral radiometer, and preferably includes miniaturized microbolometers. These devices have the advantage that cryogenic cooling of the infrared detectors is not required. However, other embodiments may include any suitable digital infrared camera.

The digital infrared cameras 14 record overlapping thermal images of the surface of a composite material 16. For example, in a preferred embodiment of the invention, the digital infrared cameras 14 each have a camera field including an array 128 pixels high by 160 pixels wide. In this embodiment, in order to configure the digital infrared cameras 14 to include a one-tenth of an inch overlap between the fields of each pair of adjacent digital infrared cameras 14, the digital infrared cameras 14 are placed at a distance from the surface of the composite material 16 such that the angle of each individual camera view includes a width of 3.2 inches at the composite material 16 surface. This provides for an effective camera field width of three inches. Thus, each pixel records an image from a space or area of the composite material 16 surface that is 0.020 inch wide. In use with a composite material 16 sheet width of 24 inches, for example, eight digital infrared cameras 14 are configured to span the entire width of the composite material 16 sheet.

In this exemplary embodiment, the image area for each individual pixel is square; thus, the 128 pixel height of a camera field in this installation spans 2.56 inches of the composite material 16 surface. With a one-tenth of an inch overlap, the effective camera field is 2.46 inches high per frame. Thus, for example, for an automated composite material layup device 12 speed of ten inches per second, the digital infrared cameras 14 are triggered every 0.246 seconds, resulting in a frame speed of approximately 4.065 frames per second.

The digital image data is sent from the digital infrared cameras 14 to an image analyzer 18, by way of an electronic link 20. The image analyzer 18, or image processor, receives the digital thermal image data and processes the data to locate material edges, foreign objects under the surface of the material, or other material anomalies, such as wrinkles. The image analyzer 18 also aggregates the digital images from the multiple digital infrared cameras 14 to form a continuous virtual digital image. In a preferred embodiment of the invention, the image analyzer 18 is capable of analyzing thirty digital image frames per second. Thus, this embodiment requires multiple image analyzers 18 in order to process the digital images from the eight digital infrared cameras 14 in the exemplary embodiment above. In this embodiment, each image analyzer 18 is capable of processing the digital images from up to three digital infrared cameras 14, requiring a total of three image analyzers 18. The excess processing capability of each image analyzer 18 is used to make manufacturing tool 17 related measurements.

The image analyzer 18 is coupled to a processor 22 by an electronic link 24, by which the digital image data may be stored in the processor 22 or in a separate memory device. In the embodiment shown in FIG. 1, the processor 22 includes a common personal computer (PC). However, in other embodiments the processor may include any suitable computing device, such as a server, a collection of networked servers or personal computers, a mainframe computer, a Personal Digital Assistant (PDA), or the like. The digital image data also may be displayed on a display 26. The display 26 shown in FIG. 1 includes a common PC monitor; however, in other embodiments, the display interface may include any suitable operator interface device.

Figure 2:
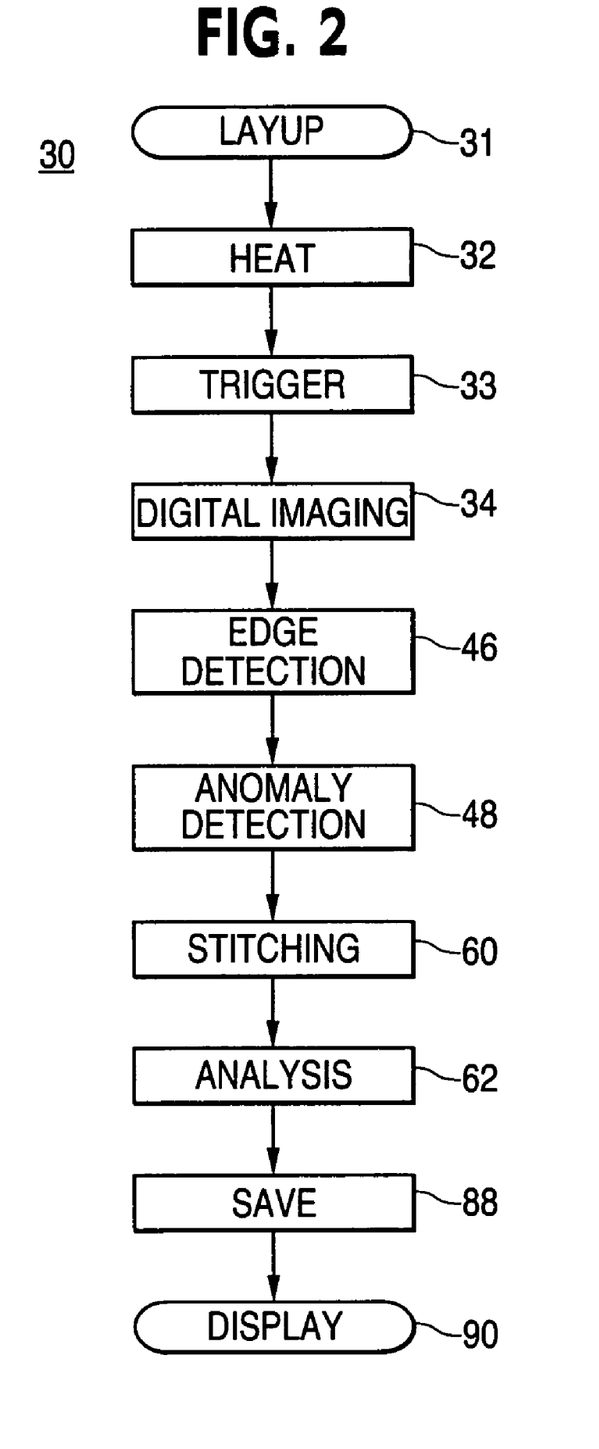
FIG. 2 is a flowchart illustrating a real-time thermal imaging method suitable for carrying out the functions of an embodiment of the invention.

A flowchart representing an embodiment of the present inventive method 30 is illustrated in FIG. 2. The RTTI process begins with the automated layup of a composite material 16 by an automatic composite material layup device 12 in step 31. Then, in step 32, heat is transferred to or from the composite material 16. A trigger is produced in step 33 to signal the digital infrared cameras 14 to digitally image the composite material surface 16 in step 34.

The process then continues with the edge detection step 46. A particularly critical area of the composite material is the transition region where one layer of material is adjacent to or overlays the edge of a previous layer. The location of these edges must meet relative positional requirements that limit the acceptable gap or overlap, as well as absolute tool related position requirements. In the edge detection step 46, the RTTI system 10 identifies the location of an edge of the composite material 16, if an edge is within the camera view. The image analyzer 18 further performs anomaly detection in step 48 to identify material defects, disbonds, wrinkles and foreign object inclusions, and aggregates or "stitches" together individual images in step 60. The image data is saved in step 88 and is displayed in step 90.

In various embodiments, different methods of transferring heat in step 32 to or from the composite material 16 are used. For example, in one embodiment, heat is conducted to or from the surface of the composite material 16 by way of a heated or cooled pressure pad on the automated composite material layup device 12 as the composite material 16 is laid down on the manufacturing tool 17. In other embodiments, heat may be applied to the surface of the composite material 16 by way of radiation or forced convection. In one embodiment, an evaporative spray is applied to the surface of the composite material 16 in order to produce a cooling effect. Furthermore, in some embodiments, the composite material 16 is heated or cooled before being laid upon the manufacturing tool 17, whereas in other embodiments, the manufacturing tool may be heated or cooled before the composite material 16 is placed on it. Thus, although the heating step 32 is shown after the layup step 31 in the embodiment shown in FIG. 2, other embodiments of the invention may include the heat step 32 in the layup process 31 or before the layup step 31.

Next, a digital image is triggered in step 33. In a preferred embodiment of the invention, a first trigger 33 is signaled at the start of a new material layup process to capture the initial cut end of the composite material 16. Images are then triggered 33 at regular time intervals representing a distance traveled by the automated composite material layup device 12. A final digital image is triggered 33 at the end of a strip of composite material 16 to capture the final cut end of the composite material 16. In addition, an operator may trigger 33 additional images at selected times during the process.

Figure 3:
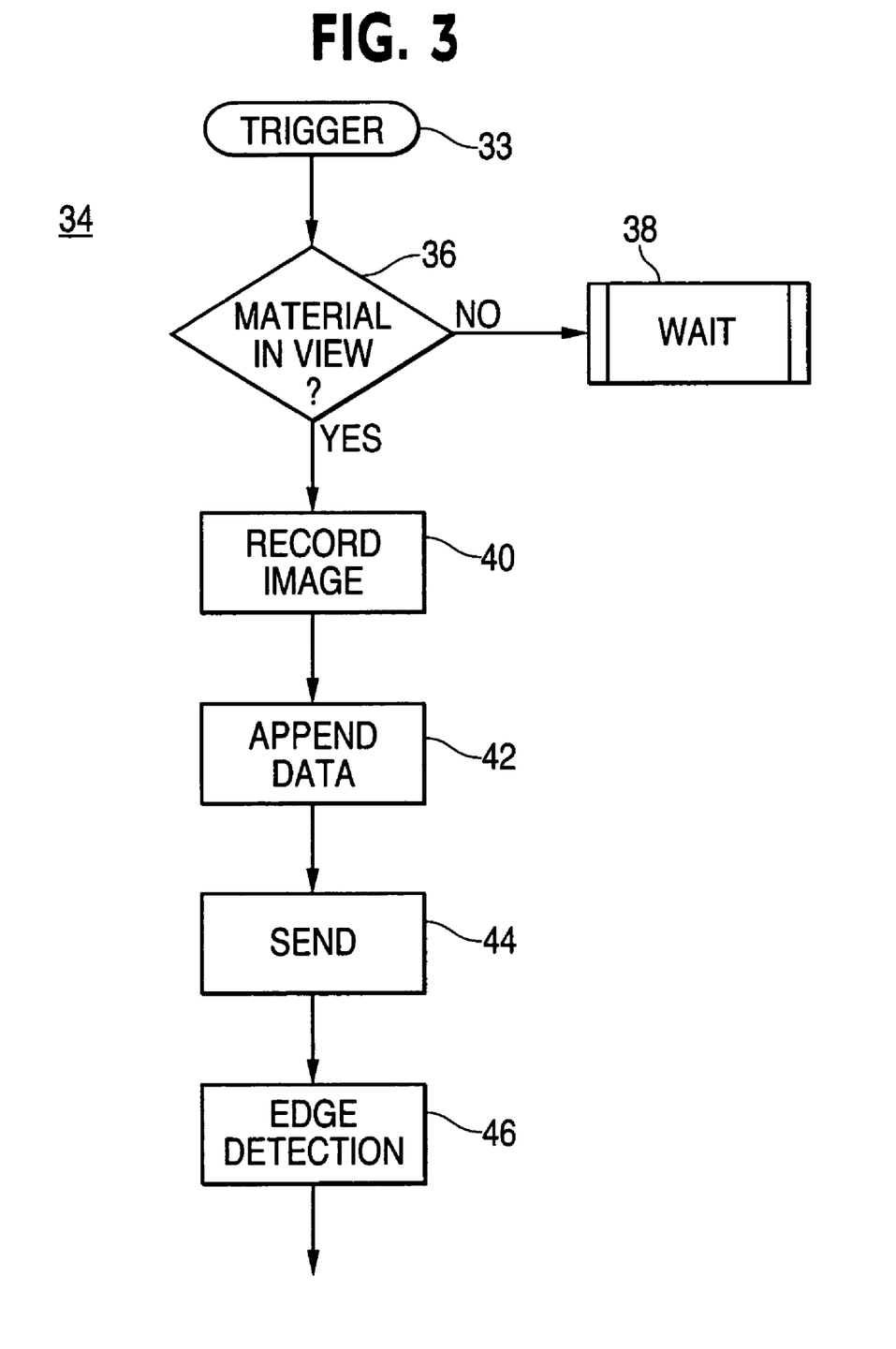
FIG. 3 is a flowchart illustrating the digital imaging step of the method of FIG. 2.

The digital infrared cameras 14 record digital images of the composite material 16 upon receiving the trigger 33 in the digital imaging step 34. A detailed flowchart of the digital imaging step 34 is depicted in FIG. 3. Upon receiving a trigger 33, the real-time thermal imaging system 10 determines whether the composite material 16 is in view of each digital infrared camera 14 in step 36. If the composite material 16 is not within the view of a particular camera 14, the system waits in step 38 for the next trigger 33. If the composite material is within the view of a particular digital infrared camera 14, the camera 14 records an image in step 40 of the composite material 16 surface. In step 42, data regarding the location of the image or images, the composite material 16 type, the surface type, the speed at which the automated composite material layup device 12 was moving at the time that the digital images were recorded, information regarding the heat application to the composite surface 16, and the like is appended to the image data, which is formatted into a set of image data frames. The image data frames are sent in step 44 to the image analyzer 18.

Figure 4:
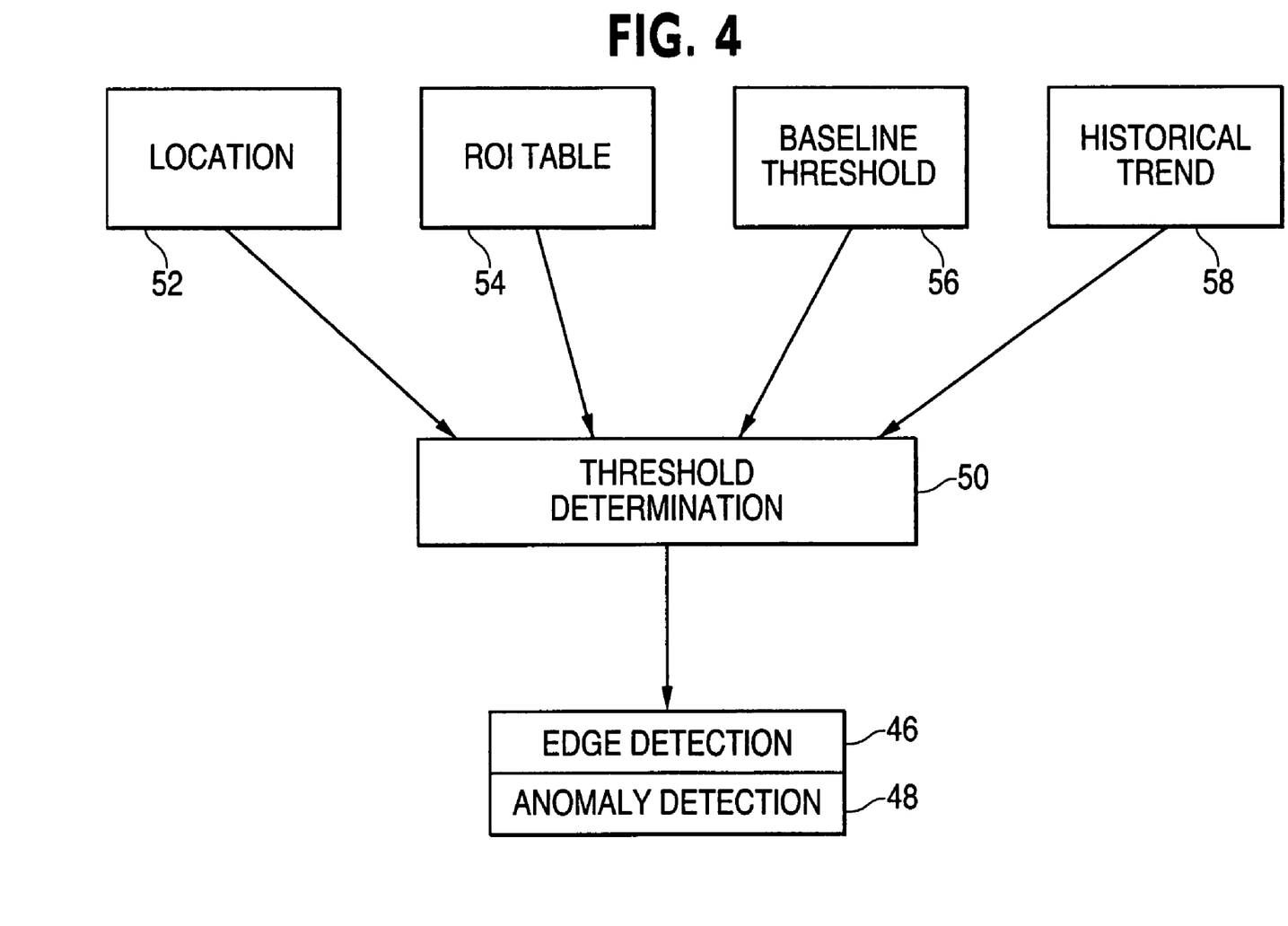
FIG. 4 is a flowchart illustrating a threshold determination method in accordance with the method of FIG. 2.

As shown in FIG. 4, in order to perform edge detection 46 and anomaly detection 48, the image processor 18 must first perform imaging filtering and enhancement. This includes image alignment, gray scale morphing, pixel intensity summation in directions of interest, and a threshold determination in step 50. The threshold determination sets threshold limits for the digital image data in order to recognize composite material 16 edges or anomalies in the composite material 16. Typically, each pixel in a digital image is represented by a gray level value; for example, a binary number between 0 and 256 may represent differing levels of spectral radiation from the composite surface 16. A threshold limit is an absolute value or a differential value that the image analyzer recognizes as an edge or an anomaly.

Threshold limits must be determined based on the location 52 where the digital image was taken, a region of interest (ROI) table 54, a set of baseline thresholds 56, and historical trend information 58. The location 52 information regarding where the digital image was taken is appended to the digital image data in step 42 of FIG. 3 and sent in step 44 to the image analyzer 18. The ROI table 54 is stored in the image analyzer 18, and includes information regarding the configuration of the composite material 16 fabrication process. For example, an ROI might include an area within a camera view at a particular location that is expected to include a composite material 16 edge. As a second example, an ROI might represent an area within the view of a digital infrared camera 14 where a composite material 16 edge of an underlying layer of composite material 16 is expected. As a third example, an ROI might include an area within the view of a particular digital infrared camera 14 of the central section of a strip of the composite material 16 that lies directly upon a manufacturing tool 17 surface or that lies over a previous layer of composite material 16.

Each ROI is associated with a threshold or a group of thresholds used in edge detection 46 or anomaly detection 48. Baseline thresholds 56, or baseline levels for each of the thresholds, are contained in the image analyzer 18 and are used as default initial values in the threshold determination process 50. The image analyzer 18 also uses historical trend information 58 regarding the gray level values of recent digital image data to adjust the thresholds during the threshold determination 50. The results of the threshold determination 50 are then used in edge detection 46 and anomaly detection 48.

Referring once again to FIG. 2, in the edge detection 46 and anomaly detection 48 steps the image analyzer 18 analyzes each pixel of each digital image frame received from the infrared cameras 14 to determine if the pixel is beyond the threshold or thresholds associated with the region of interest (ROI) 54 associated with the location 52 of the digital image. Although the term "beyond" is used here, it will be recognized that a given threshold value may be a maximum or a minimum, and that a corresponding value beyond a threshold may be greater than or less than the threshold value, depending on the specific threshold definition.

The image analyzer 18 is a dedicated processor designed to analyze digital images. In a preferred embodiment of the invention, the image analyzer 18 is capable of processing up to thirty images per second. Features of the image analysis are defined by software. An example of a software application compatible with an embodiment of the invention is Lab-VIEW, produced by National Instruments Corp. of Texas, USA, which in a preferred embodiment of the invention has been modified to provide additional real-time processing capabilities. Software modules provide for data logging, supervisory control, historical display and other control features.

The image analyzer 18 then aggregates the individual digital images from the various digital infrared cameras 14 and from sequential time periods representing sequential locations along the composite material 16 into a continuous virtual digital image in a process known as stitching 60. In the stitching process, the image analyzer 18 compares adjacent digital images, either from adjacent digital infrared cameras 14 or from time sequential images from a single digital infrared camera 14 to identify matching pixels within digital image frames from the adjacent digital images. The image analyzer thus aligns matching pixels in adjacent digital images in order to align the adjacent images with each other, creating a continuous digital image. By repeating this process with adjacent digital images from different cameras and from a time sequence, the image analyzer 18 is able to aggregate the digital images into a continuous virtual digital image representing the composite surface 16.

In the embodiment shown in FIG. 2, the stitching process 60 is shown after the edge detection 46 and anomaly detection 48 steps and before the analysis step 62. However, in other embodiments, the stitching 60 process may occur before the edge detection 46 or anomaly detection 48 steps, or after analysis 62, depending on the requirement of the edge detection 46, anomaly detection 48 and analysis 62 steps. Furthermore, in alternative embodiments, the stitching 60 process may be performed on a real-time basis or may be performed at a later time. For example, in an embodiment, the image analyzer 18 performs edge detection 46 and anomaly detection 48 and analyzes the results 62 within each digital image on a real-time basis, but performs stitching at a later time to further analyze edges or anomalies discovered in the edge detection 46 and anomaly detection 48 steps during a subsequent analysis 62.

Figure 5:
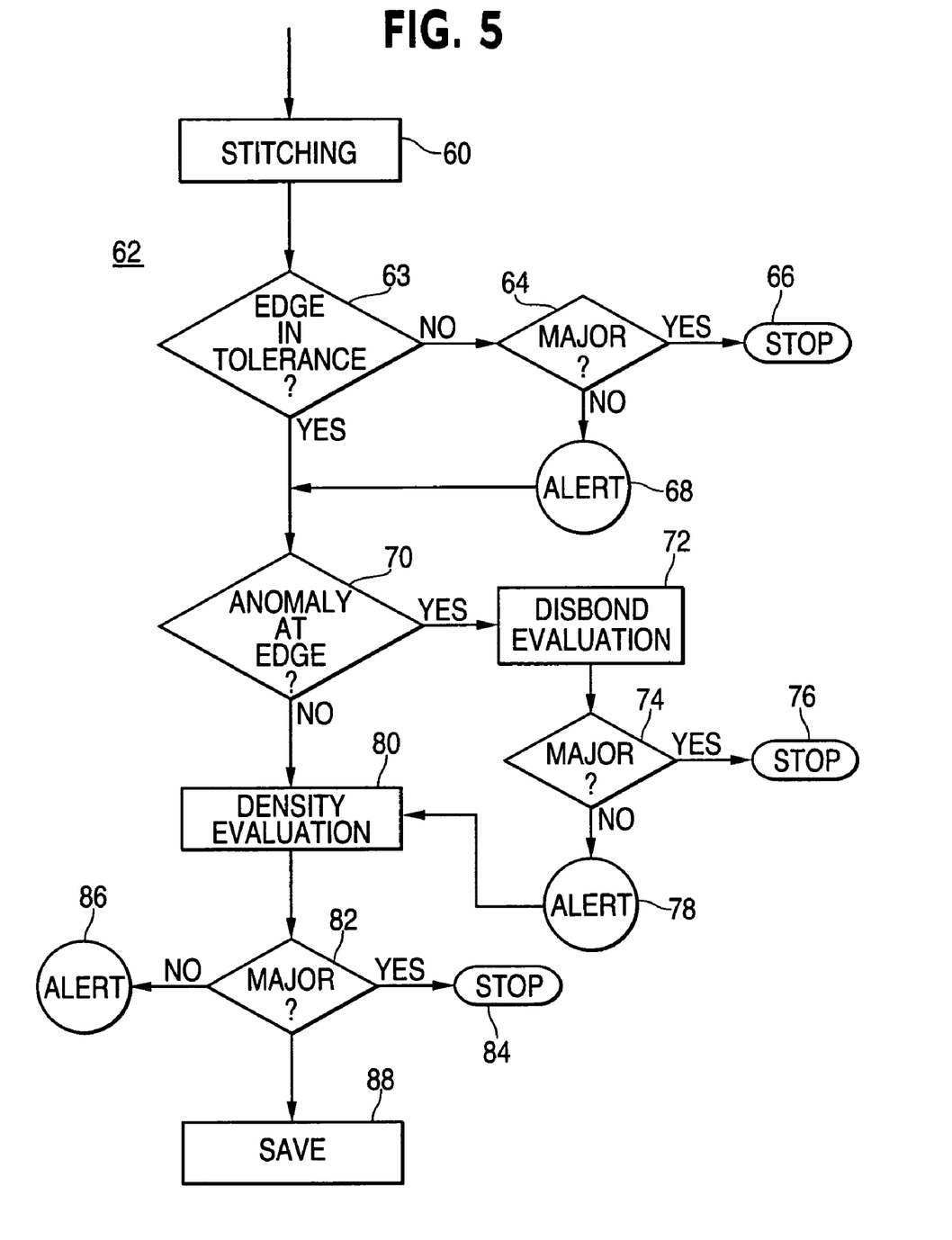
FIG. 5 is a flowchart illustrating the Analysis step of the method of FIG. 2.

A detailed flowchart of the analysis 62 step of FIG. 2 is shown in FIG. 5. In step 63, the image analyzer 18 evaluates the locations of the image data pixels whose gray level values are beyond an edge threshold to determine if the composite material 16 edge is within tolerance. This process may include multiple tolerance levels represented by multiple ROIs 54. For example, in a preferred embodiment of the inventive method, the image analyzer 18 determines if the edge is outside a minor tolerance ROI or a major tolerance ROI in step 64. If the edge is outside a major tolerance ROI, the image analyzer 18 generates a signal to send to the automated composite material layup device 12 to stop the layup process in step 66. If, on the other hand, the edge is outside a minor tolerance ROI but inside a major tolerance ROI, the image analyzer 18 instead generates an alert signal in step 68. For example, the image analyzer 18 may send the alert signal to illuminate a lamp on an operator panel, or send the alert signal to the processor 22 to display an alert message on the display 26. In addition, the image analyzer 18 may generate a control signal and send it the automated composite material layup device 12 for path or cut correction.

In step 70, the image analyzer 18 determines if any of the pixels with gray level values beyond an anomaly threshold value associated with the ROI 54 in which the pixels are located are near an edge of the composite material 16. If so, the image analyzer 18 performs a disbond evaluation 72 to determine if the affected area is within tolerance based on the surface area of the anomaly, the number of anomalies within a unit area, and the distance between or proximity of anomalies. In a preferred embodiment, if the composite material 16 disbond is outside of tolerance, the image analyzer 18 further determines whether the disbond is outside a major tolerance or a minor tolerance in step 74. If the disbond is outside a major tolerance, the image analyzer generates a signal to send to the automated composite material layup device 12 to stop the layup process in step 76. Otherwise, if the anomaly is outside of a minor tolerance but within a major tolerance, the image analyzer 18 generates an alert signal in step 78 to alert an operator that the composite material 16 layup process is out of tolerance.

Next, the image analyzer 18 performs a density evaluation 80 as shown in FIG. 5. For example, in a preferred embodiment of the invention, the image analyzer 18 evaluates the number of anomalies detected over a unit area of the composite material 16 surface and compares the anomaly density to an anomaly density threshold. If the density, or number of anomalies per unit area, is greater than a major threshold, determined in step 82, the image analyzer 18 generates a signal to send to the automated composite material layup device 12 to stop the composite material 16 layup process in step 84. Otherwise if the image analyzer 18 determines that the anomaly density is beyond a minor threshold, but within a major threshold, the image analyzer 18 generates an alert signal in step 86. Once again, in a preferred embodiment of the invention, the alert signal may be sent to illuminate a lamp on an operator panel, or to the processor 22 to show an alert message on the display 26.

Returning to FIG. 2, in step 88 the image analyzer 18 sends the digital image data combined with the results of the analysis to the processor 22 to be saved. This digital data may be saved in the processor 22 memory, or the processor 22 may save the digital data in a separate memory device. In an alternative embodiment, the image analyzer 18 sends the digital data directly to an independent memory device. The system also displays the digital data as an overlaid image in step 90 of FIG. 2.

Figure 6:
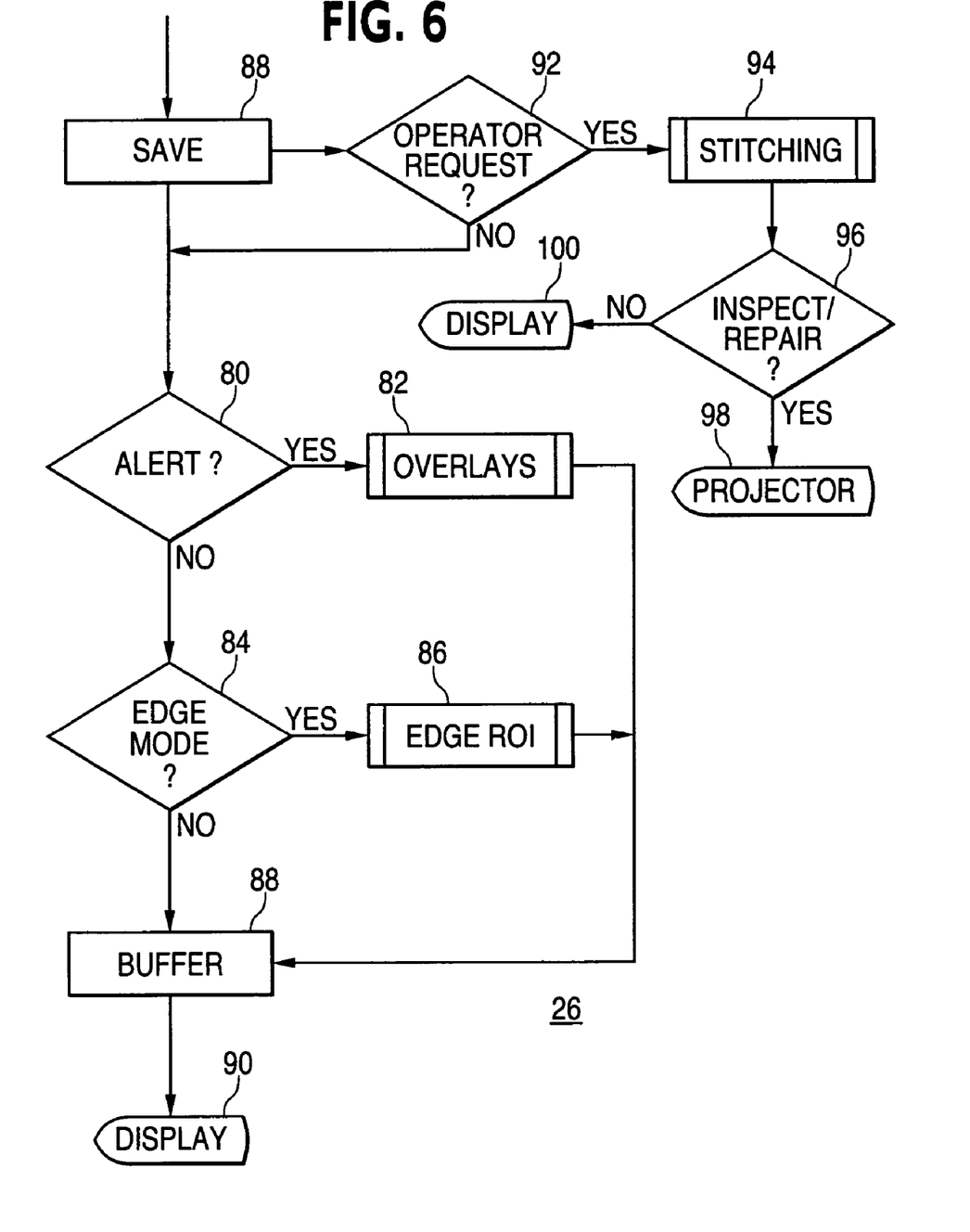
FIG. 6 is a flowchart illustrating the Display step of the method of FIG. 2.

A detailed flowchart of the display step 90 is shown in FIG. 6. Because the digital images are stored with appended data regarding the time and location of the image on the composite material 16 surface, an operator may request display of historical digital data and images. The request may be made from a hardwired central location or from one or more wireless devices which would allow an operator to view images on the wireless device in addition to requesting projection of information onto the composite surface. In step 92, the RTTI system 10 determines whether an operator has requested that a digital image be displayed. If so, the image analyzer 18 performs a stitching operation in step 94 to aggregate two or more digital images, if necessary to perform the operator request, and sends the image to an operator associated display in step 100.

The RTTI system 10 then determines whether the operator request includes an inspect or repair request in step 96. If so, the digital image data is sent to a laser or image projector in step 98 for projection onto the composite material surface 16 at the location on the surface which the images represent. In a preferred embodiment of the invention, the digital image data is projected onto the composite material surface 16 using a laser projector. In other embodiments, the image may be projected onto the composite material surface 16 using any suitable projection device, including a digital image projector.

During normal operation, when no operator request has been received in step 92, the RTTI system 10 determines on a continuing basis whether there has been an alert signal in step 80. If so, in step 82 the image analyzer 18 overlays associated region of interest (ROI) 54 and anomaly or material edge information onto the digital image containing the pixels associated with the alert signal. The digital image with overlays is then sent to a display buffer in step 88. If no alert signal has been generated in step 80, then the RTTI system 10 determines whether the digital image includes a composite material 16 edge in step 84. If so, the image analyzer 18 overlays the associated edge ROI onto the digital image in step 86. Then the digital image is sent to the display buffer in step 88 for display on the display 26 in step 90.

In a preferred embodiment, the RTTI system 10 includes multiple displays 26 in order to display on a continuous basis the digital images from each of the digital infrared cameras 14 during the composite material 16 layup process. In other embodiments, the RTTI system 10 may include any number of displays 26 to display real-time digital image data, or historical digital image data, or ROI information data, threshold data or any other data regarding the RTTI process.

In addition, in a preferred embodiment of the invention, the RTTI 10 system prioritizes the display of digital image data according to whether an alert signal has been generated, whether the digital image includes a composite material 16 edge, or whether the digital image contains any anomalies. For example, in an embodiment digital display data including pixels associated with an alert signal are given first priority for display, digital images that include a composite material 16 edge are given second priority, and other digital images are given third priority. The RTTI system 10 stores recent digital image data in a display buffer, in step 88 in FIG. 6, with the associated priority information for display.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A nondestructive in-process inspection method for automated composite material layup, comprising the steps of:
    generating a first control signal to control a digital infrared camera;
    sending the first control signal to the digital infrared camera;
    digitally imaging an infrared spectral radiance of an area of a surface of a composite material; and
    sending an image data frame to an image analyzer, the image analyzer performing the steps of:
        accessing a region of interest (ROI) table, the ROI table including information associated with the composite material and a fabrication process;
        defining a region of interest (ROI) associated with the surface of the composite material in response to information accessed from the ROI table, wherein the ROI includes an underlying edge of composite material based on the information accessed from the ROI table;
        determining a threshold value associated with the region of interest, and
        analyzing the image data frame to compare a gray level value to the threshold value.

2. The nondestructive in-process inspection method of claim 1, further comprising the steps of:
    generating a second control signal based on the comparison of the gray level value with the threshold value; and
    sending the second control signal to a composite material placement device controller.

3. The nondestructive in-process inspection method of claim 1, further comprising the step of generating an alert signal based on the comparison of the gray level value with the threshold value.

4. The nondestructive in-process inspection method of claim 1, further comprising the step of the image analyzer performing the step of determining a location of a material edge based on the comparison of the gray level value with the threshold value, wherein the region of interest is a material edge ROI, and the threshold value is a material edge threshold value.

5. The nondestructive in-process inspection method of claim 4, further comprising the steps of:
    the image analyzer further performing the steps of:
        defining an edge tolerance zone associated with the material edge ROI, and
        determining whether the location of the material edge is within the edge tolerance zone;
    generating a second control signal based on the material edge being outside the edge tolerance zone in a first direction; and
    sending the second control signal to a composite material placement device controller, thereby signaling the composite material placement device controller to command the composite material placement device to steer in a second direction.

6. The nondestructive in-process inspection method of claim 4, further comprising the steps of:
    the image analyzer further performing the steps of:
        defining an edge tolerance zone associated with the material edge ROI,
        determining whether the location of the material edge is within the edge tolerance zone, and
        generating an alert signal based on the material edge being outside the second edge tolerance zone; and
    alerting an operator in response to the alert signal.

7. The nondestructive in-process inspection method of claim 4, further comprising the steps of:
    the image analyzer further performing the steps of:
        defining an edge tolerance zone associated with the material edge ROI, and
        determining whether the location of the material edge is within the edge tolerance zone;
    generating a second control signal based on the material edge being outside the edge tolerance zone; and
    sending the second control signal to a composite material placement device controller, thereby signaling the composite material placement device controller to command the composite material placement device to halt operation.

8. The nondestructive in-process inspection method of claim 1, further comprising the step of the image analyzer performing the step of determining a location of an anomaly in the region of interest based on the comparison of the gray level value with the threshold value, wherein the threshold value is an anomaly threshold value.

9. The nondestructive in-process inspection method of claim 8, wherein the region of interest is an edge ROI, further comprising the steps of:
    the image analyzer further performing the steps of:

determining an individual anomaly surface area limit associated with the region of interest, determining a surface area of the anomaly, and generating an alert signal based on the surface area of the anomaly exceeding the anomaly surface area limit; and alerting an operator in response to the alert signal.

10. The nondestructive in-process inspection method of claim 8, wherein the region of interest is an edge/lap ROI, further comprising the steps of:

the image analyzer further performing the steps of:

determining an individual anomaly surface area limit associated with the region of interest, and determining a surface area of the anomaly;

generating a second control signal based on the surface area of the anomaly exceeding the anomaly surface area limit; and sending the second control signal to a composite material placement device controller, thereby signaling the composite material placement device controller to command the composite material placement device to halt operation.

11. The nondestructive in-process inspection method of claim 8, further comprising the steps of:

the image analyzer further performing the steps of:

determining an anomaly density limit associated with the region of interest, determining a plurality of locations of a plurality of anomalies in a region of interest, counting the plurality of anomalies, evaluating the anomaly density based on a number of anomalies in a unit area; and generating an alert signal based on the anomaly density exceeding the anomaly density limit; and alerting an operator in response to the alert signal.

12. The nondestructive in-process inspection method of claim 8, further comprising the steps of:

the image analyzer further performing the steps of:

determining an anomaly density limit associated with the region of interest, determining a plurality of locations of a plurality of anomalies in a region of interest, counting the plurality of anomalies, and evaluating the anomaly density based on a number of anomalies in a unit area;

generating a second control signal based on the anomaly density exceeding the anomaly density limit; and sending the second control signal to a composite material placement device controller, thereby signaling the composite material placement device controller to command the composite material placement device to halt operation.

13. The nondestructive in-process inspection method of claim 8, further comprising the steps of:

the image analyzer further performing the steps of:

determining an anomaly proximity limit associated with the region of interest, determining the location of a first anomaly in the region of interest based on the comparison of the gray level value with the threshold value, wherein the threshold value is an anomaly threshold value, determining the location of a second anomaly in the region of interest based on the comparison of the gray level value with the anomaly threshold value, determining a proximity of the first anomaly to the second anomaly, and generating an alert signal based on the proximity of the first anomaly to the second anomaly exceeding the anomaly proximity limit; and alerting an operator in response to the alert signal.

14. The nondestructive in-process inspection method of claim 8, further comprising the steps of:

altering an image data frame in order to virtually highlight an area of an image; and projecting a representation of the highlighted image onto the corresponding area of the surface of the composite material to identify the location of an anomaly.

15. The nondestructive in-process inspection method of claim 1, further comprising the steps of:

the image analyzer further performing the steps of:

determining an anomaly proximity limit associated with the region of interest, determining the location of a first anomaly in the region of interest based on the comparison of the gray level value with the threshold value, wherein the threshold value is an anomaly threshold value, determining the location of a second anomaly in the region of interest based on the comparison of the gray level value with the anomaly threshold value, and determining a proximity of the first anomaly to the second anomaly;

generating a second control signal based on the proximity of the first anomaly to the second anomaly exceeding the anomaly proximity limit; and sending the second control signal to a composite material placement device controller, thereby signaling the composite material placement device controller to command the composite material placement device to halt operation.

16. The nondestructive in-process inspection method of claim 1, further comprising the steps of:

sending a plurality of image data frames to the image analyzer, the image data frames including a first image and a second image, wherein a first set of image data frames of the first image and a second set of image data frames of the second image represent a same portion of the surface of the composite material; and the image analyzer further performing the step of aggregating the first and second images to form a single continuous virtual image of the composite material surface, wherein the first set of image data frames align with the second set of image data frames.

17. The nondestructive in-process inspection method of claim 1, further comprising the steps of:

generating a second control signal to control a second digital infrared camera;

sending the second control signal to the digital infrared camera;

sending a first image from the first digital infrared camera to the image analyzer, the first image including a first set of image data frames; and sending a second image from the second digital infrared camera to the image analyzer, the second image including a second set of image data frames, wherein the first set of image data frames of the first image and the second set of image data frames of the second image represent a same portion of the surface of the composite material; and the image analyzer further performing the steps of aggregating the first and second images to form a single continuous virtual image of the composite material surface, wherein the first set of image data frames align with the second set of image data frames.

18. The nondestructive in-process inspection method of claim 1, further comprising the step of projecting an alignment pattern onto the surface of the composite material for aligning a plurality of aggregate images.

19. The nondestructive in-process inspection method of claim 1, further comprising the step of the image analyzer further performing the step of evaluating a plurality of historical gray level values associated with a plurality of historical image data frames in order to determine the threshold value.

20. The nondestructive in-process inspection method of claim 1, further comprising the step of heating the surface of the composite material a predetermined time period before sending the first control signal to the digital infrared camera.

21. The nondestructive in-process inspection method of claim 1, further comprising the step of converting the gray level value recorded by the digital infrared camera into a temperature value.

22. The nondestructive in-process inspection method of claim 1, further comprising the step of altering an image data frame in order to virtually overlay a representation of the region of interest on an image.

23. The nondestructive in-process inspection method of claim 1, further comprising the step of sending the image data frame to a display device for display.

24. The nondestructive in-process inspection method of claim 1, further comprising the step of projecting a representation of the region of interest onto the corresponding area of the surface of the composite material.

25. A nondestructive in-process inspection method for automated composite material layup, comprising the steps of:
   receiving an infrared spectral radiance of an area of a surface of a composite material;
   accessing a region of interest (ROI) table, the ROI table including information associated with composite material and fabrication process;
   defining a region of interest (ROI) associated with the surface of the composite material in response to information accessed from the ROI table, wherein the ROI includes an underlying edge of composite material based on the information accessed from the ROI table;
   determining a threshold value associated with the ROI; and
   analyzing the image data frame to compare a gray level value to the threshold value.

\* \* \* \* \*